US005674837A

United States Patent [19]
Kirkpatrick et al.

[11] Patent Number: 5,674,837
[45] Date of Patent: Oct. 7, 1997

[54] STABLE BLEOMYCIN SULFATE SOLUTION SUITABLE FOR INJECTION

[75] Inventors: Gayle A. Kirkpatrick; Pramod K. Gupta, both of Gurnee, Ill.

[73] Assignee: Abbott Laboratories, Abbott Park, Ill.

[21] Appl. No.: 283,452

[22] Filed: Aug. 1, 1994

[51] Int. Cl.$^6$ .................. C07K 14/36; A61K 31/00
[52] U.S. Cl. .............................. 514/8; 530/322
[58] Field of Search ................... 530/322; 514/8

[56] References Cited

PUBLICATIONS

Meyers et al., "Preparation . . . Bleorycin", J. Nucl. Med., vol. 16(9) Sep. 835–8 (1975). Abstract.

Yokoyama et al., "The importance . . . 99mTC Sleorycin", Int. J. Appl. Radiat. Isof., vol. 2 (9–10) pp. 549–555 (1978). Abstract.

Adams, et al., American Journal of Hospital Pharmacy; "Instability of Bleomycin in Plastic Containers", vol. 39, pp. 1636, published Oct., 1982.

Aszalos, et al., Journal of Pharmaceutical Sciences; "High–Performance Liquid Chromatographic Determination of Components of Bleomycin Preparations", vol. 70, No. 8, pp. 878–880, published Aug. 1981.

Benvenuto, et al., American Journal of Hospital Pharmacy; "Stability Compatibility of Antitumor Agents in Glass and Plastic Containers", vol. 38, pp. 1914–1918, published Dec. 1981.

Crooke, et al., Journal of Medicine; "Bleomycin, A Review", vol. 7, No. 5, pp. 333–339, published 1976.

Dalton–Bunnow, et al., American Journal of Hospital Pharmacy, "Update on room–temperature stabiltiy of drug products labeled for refrigerated storage", vol. 47, pp. 2522–2524, published Nov. 1990.

Dorr, et al., Journal of Medicine, "Bleomyicn Compatibility with Selected Intravenous Medications", vol. 13, Nos. 1&2, pp. 121–130, published 1982.

Koberda, et al., American Journal of Hospital Pharmacy, "Stability of bleomycin sulfate reconstituted in 5% dextrose injection or 0.9% sodium chloride injection stored in glass vials or polyvinyl chloride containers", vol. 47, pp. 2528–2529, published Nov., 1990.

MeadJohnson, Oncology Products, "Blenoxane® Sterile, Bleomycin sulfate", USP, published Mar., 1988.

Trissel LA, et al., Handbook of Injectable Drugs, American Society of Hospital Pharmacists, Bethesda, MN, pp. 69–72, published 1986.

D'Arcy, PF, Letter, Comment on handling of anticancer drugs, Drug Intelligence and Clinical Pharmacy, 18, p. 417, published 1984.

Travenol Laboratories, Inc., "TCX Premix Chemical Stability Dting", published Aug. 26, 1987.

*Primary Examiner*—Cecilia J. Tsang
*Assistant Examiner*—Lynn Touzeau
*Attorney, Agent, or Firm*—David C. Hannum; Brian R. Woodworth

[57] ABSTRACT

A method of stabilizing bleomycin solutions and to the stable bleomycin solutions resulting therefrom are described. In the method described, bleomycin solution is stabilized by solubilizing bleomycin powder in an aqueous solution and storing the solution at reduced temperature while it awaits use.

4 Claims, No Drawings

STABLE BLEOMYCIN SULFATE SOLUTION SUITABLE FOR INJECTION

BACKGROUND OF THE INVENTION

1. Technical Field

The present invention relates to a stable bleomycin solution and to a method of stabilizing bleomycin in solution form. More specifically, the invention relates to solubilizing bleomycin powder in an aqueous solvent suitable for injection and storing such solution below room temperature prior to use.

2. Prior Art

Bleomycins are a family of glycopeptide antibiotics obtained from the fermentation broth of *Streptomyces verticillus*. Bleomycins (as the sulfate or hydrochloride) are used therapeutically for the treatment of human neoplasms, particularly squamous cell carcinoma, sarcoma, and malignant lymphoma (Sakai, 1978). As available commercially, the drug consists of thirteen chromatographically separable fractions, including bleomycin $A_2$, bleomycin $B_2$, and various minor subfractions such as bleomycin $A_5$, $B_1$, $B_4$ and bleomycinic acid. Dorr, R. T., Peng, Y. and Alberts, D. S., *Journal of Medicine*, Vol. 13 (Nos. 1 & 2): 121–103 (1982). Among the minor components of bleomycin, $B_4$ is the most toxic.

Bleomycin is available in the U.S. as U.S.P. grade bleomycin sulfate and measured as containing 90.0–120.0% of the labeled amount of bleomycin. Bleomycin sulfate has a potency of 1.5–2.0 bleomycin units per mg and contains 60–70% bleomycin $A_2$, 25–32% bleomycin $B_2$ and not more than 1% bleomycin $B_4$. Not less than 90% of the total content is bleomycin $A_2$ and $B_2$.

Commercially available preparations of bleomycins are marketed in powder form to overcome the problem of having a limited shelf life in solution. Blenoxane® (bleomycin sulfate) for example, is reported to be stable in solution for 24 hours at room temperature in sodium chloride (Physician's Desk Reference, Edition 48, 1994). Dorr et al. however, have reported that bleomycin in saline is stable for up to seven days (*Journal of Medicine*, Vol. 13 (Nos. 1 & 2): 121–103 (1982)). Reconstituted solutions of bleomycin have also been reported to be stable for 2 weeks at room temperature and 4 weeks at 2° C.–8° C. (Trissel L. A., et al. Handbook of Injectable Drugs, American Society of Hospital Pharmacists, Bethesda, Minn., 1985 edition). Another reference quotes Nippon Kayaki Co., Ltd., the manufacturer of bleomycin hydrochloride as claiming that "the potency is not reduced for a period of at least one year when it is kept in physiological saline solution at normal temperature" (D'Arcy, P. F. Letter, comment on handling of anticancer drugs, Drug Intelligence and Clinical Pharmacy, Vol. 18:417 (1984)). Another manufacturer, offering bleomycin as a multidose premix in sodium chloride, claims stability for 100 days under refrigeration (Travenol Laboratories, Inc., "TCX Premix Chemical Stability Dating", Aug. 26, 1987).

Koberda et al. have reported on the stability of Blenoxane reconstituted in a 5% dextrose solution or in 0.9% sodium chloride and stored at room temperature in both glass vials and polyvinyl chloride containers (*American Journal of Hospital Pharmacy*, Vol. 47:2528–2529 (1990)). Although their results indicate that glass vials are better than polyvinyl chloride containers for maintaining stability, the testing period of the bleomycin solution did not exceed 34 hours.

Bleomycin has also been incorporated in several ointment bases. It has been reported as being stable in petrolatum, losing only 7% of its activity in two years, but quite unstable in dermabase or tincture of benzoin (*Journal of Medicine*, Vol. 7 (No. 5): 338 (1976)).

In view of the above referenced reports, it is apparent that there is a need for stable solutions of bleomycin. To the best of our knowledge however, no commercial offering has been made of such a product. There has now been discovered a method for the long term stabilization of bleomycin in solution form. An advantage of the product obtained by this method over the current product is the elimination of the reconstitution step, which decreases the potential hazard to the health care provider who prepares the drug for use. Minimizing the exposure of the health care provider to this drug is critically important in light of its reported toxicity. Another advantage provided by this method is the reduction in cost of preparing the drug, since the need for lyophilization or powder fill is eliminated.

SUMMARY OF THE INVENTION

The present invention provides a method for stabilizing bleomycin solutions and to the stable bleomycin solutions resulting therefrom. The method comprises the steps of solubilizing bleomycin powder at the manufacturing site, in an aqueous solution and storing the aqueous solution generally from 2° C.–15° C., preferably from 2° C.–8° C. and most preferably at 5° C. for periods from 1 to 24 months while it awaits use. Any aqueous solution that is suitable for solubilizing the bleomycin is appropriate, such as buffered solutions, saline, dextrose, pH adjusted water and the like.

DETAILED DESCRIPTION OF THE INVENTION

The present invention provides for a method of producing stable bleomycin solutions and to the stable composition resulting therefrom. This method comprises the steps of solubilizing bleomycin or any formulation thereof, in an aqueous solution and storing the solution below room temperature for periods from 1 to 24 months while it awaits use. The solubilization step takes place at the manufacturing site, i.e. prior to or at the time of packaging the drug thereby eliminating the need for the health care provider to reconstitute the powder form of drug at the site where it is to be administered.

As used herein, "bleomycin" refers to a group of related glycopeptides isolated from *Streptomyces verticillus*. It may also refer to bleomycin produced by chemical synthesis. Bleomycins useful in the present invention include pharmaceutical compositions comprising a mixture of bleomycin and salts. Preferred bleomycin solutions are pharmaceutical compositions of bleomycin sulfate and bleomycin hydrochloride. A particularly preferred bleomycin is bleomycin sulfate.

As used herein, "solubilizing or solubilization" refers to the dissolution of bleomycin powder in an aqueous solution. Aqueous solutions suitable for solubilization may comprise any solution suitable for dissolving bleomycin. Preferred aqueous solutions are those suitable for injection, such as water, pH adjusted water, saline, dextrose and the like. Aqueous solutions may also comprise other therapeutic compounds or drugs which are compatible with bleomycin. Most preferred solutions are water for injection and water adjusted to about pH 4.6.

As used herein, "reduced" temperatures refer to temperatures below room temperature. Reduced temperatures are generally in the range of about 2° C. to about 15° C. Preferred temperatures are in the range of about 2° C. to about 8° C. A most preferred temperature is about 5° C.

As used herein, "stable" or "stabilizing" refers to the retention of potency of a bleomycin solution in the range of about 90–120% of its initial starting potency. Potency refers to the amount of antimicrobial activity of the bleomycin solution as determined by microbial assay and is expressed in units of activity. One unit of bleomycin is equivalent in activity to 1 mg of bleomycin $A_2$ reference standard. $A_2$ reference standards are well known to those of ordinary skill in the art and may be purchased from a variety of commercial suppliers. The microbial assay used to determine potency of the drug, may be any validated microbial assay that is useful for approving drug products for human consumption. By way of illustration, a microbial assay useful in the present invention is the microbial agar diffusion assay described in 21 CFR §§436.101–103, 105 and 200 (Apr. 1, 1991 Edition). The assay is performed as follows:

1. Preparative Materials
   a. Media: Ingredients are used that conform to the standards, if any, prescribed by the USP or N.F. In lieu of preparing the media from the individual ingredients specified below, they may be made from dehydrated mixtures that, when reconstituted with distilled water, have the same composition as such media. Minor modifications of the individual ingredients specified in this section are permissible if the resulting media possess growth-promoting properties at least equal to the media described.
      i. Medium 34: 10 grams (gm) of glycerol, 10 gm of peptone, 10 gm of beef extract, and 3 gm of sodium chloride are mixed in a final volume of 1 liter of distilled water and then sterilized by autoclaving. The pH of the solution is 7.0 after sterilization.
      ii. Medium 35: This medium is prepared in the same manner as medium 34 with the addition of 17.0 gm of agar to each liter of medium.
      iii. Medium 36: 15.0 gm of pancreatic digest of casein, 5.0 gms of papaic digest of soybean, 5.0 gm of sodium chloride and 15.0 gm of agar are mixed in a final volume of 1 liter of distilled water and then sterilized by autoclaving. The pH of the solution is 7.3 after sterilization.
   b. Slants and Plates
      i. Slants: Agar slants for maintenance of test organisms are prepared using 10 milliliters (mL) of Medium 36 described above. The general method of preparing slants is well known to those of ordinary skill in the art.
      ii. Plates for potency assay: The number of plates required per assay is dependent on the number of samples to be tested. For all tests, at least 12 plates are required to establish a standard response line (see "Standard Response Line Solutions" below) and at least 3 plates are required to determine the potency of each test sample. Plates for potency testing are prepared by evenly distributing a 10 mL base layer of melted Medium 35 to an appropriate number of plastic or glass Petri dishes (20 by 100 millimeters). The layer of base agar medium is poured into each plate on a flat level surface, and a cover placed on each plate in turn; if a nonporous cover is used, the cover is left slightly ajar to prevent accumulation of condensing moisture from the hot agar base layer. After the agar hardens, the nonporous cover is seated on each plate. To prepare the seed layer, an amount of test organism suspension (see "Test Organism Suspension" below) is added to a sufficient amount of Medium 35 (which has been melted and cooled to 48° C.–50° C.) to equal a ratio of 1 mL suspension for each 100 mL of medium. The flask is swirled to obtain a homogeneous suspension, and 6 mL of suspension then added to each of the plates containing the uninoculated base agar. The seed layer is spread evenly over the agar surface, covered and allowed to harden on a flat, level surface. After the agar has hardened, 6 cylinders (stainless steel with an outside diameter of 8 millimeters (±0.1 millimeter), an inside diameter of 6 millimeters (±0.1 millimeter), and a length of 10 millimeters (±0.1 millimeter)) are placed on the inoculated agar surface so that they are at approximately 60° intervals on a 2.8 centimeter radius.
   c. Test Organism Suspension: Test organism, *Mycobacterium smegmatis* (Cat. #607 from the American Type Culture Collection, 12301 Parklawn Dr., Rockville, Md. 20852 ) is maintained on agar slants containing 10 mL of Medium 36 as described above and transferred to a fresh slant about once a week. Slants are Incubated at 37° C. for 48 hours immediately after transfer. To prepare the test organism suspension, 3 mL of sterile USP saline T.S., is used to wash the growth from the agar slant into a 500-mL Edenmeyer flask containing 100 mL of Medium 34 and 50 gm of glass beads. The culture is agitated by rotation at a speed of 130 cycles per minute and a radius of 3.5 centimeters at 37° C. for 5 days. The test organism suspension is stored under refrigeration for a period of up to 2 weeks.
   d. Solutions:
      i. Solution 16: (0.1M potassium phosphate buffer, pH 7.0) 13.6 gm dibasic potassium phosphate and 4.0 gm of monobasic potassium phosphate are mixed in a final volume of 1 liter of distilled water and then sterilized by autoclaving. After sterilization, the pH is adjusted to 6.8–7.2 with 18N phosphoric acid or 10N potassium hydroxide.
      ii. Working Standard Stock Solution: The working standard of bleomycin is prepared as follows: In an atmosphere of about 10 percent relative humidity, about 100 milligrams of a fine powder of the drug is transferred to a tared weighing bottle equipped with a ground-glass stopper. The bottle is weighed and placed in a vacuum oven, with the stopper tilted on its side so that there is no closure during the drying period. The drug is dried at a temperature of 25° C. and a pressure of 5 millimeters of mercury or less for 4 hours. At the end of the drying period, the vacuum oven is filled with air that has been dried by passing it through a drying agent such as sulfuric acid or silica gel. The stopper is replaced and the weighing bottle placed in a desiccator over a desiccating agent, such as phosphorous pentoxide or silica gel, allowed to cool to room temperature, and reweighed. The percent of loss is calculated. Then the weighed portion is dissolved and diluted in Solution 16 to a final concentration of 2 units/mL.
      iii. Standard Response Line Solutions: To prepare standard response line solutions, an aliquot of the working standard stock solution is further diluted to final concentrations of 0.01, 0.02, 0.04, 0.08, and 0.16 units/mL. The reference concentration of the assay is the mid concentration of the response line (i.e. 0.04 units/mL).

2. Procedure for the assay: For the standard response line, a total of 12 plates are used-three plates for each response line solution, except the reference concentration solution which is included on each plate. On each set of three plates, three alternate cylinders are filled with the reference concentration solution and the other three cylinders with the concentration of the response line under test. Thus, there will be 36 reference concentration zones of inhibition and nine zones of inhibition for each of the four other concentrations of the response line. For each sample tested three plates are used. Three alternate cylinders on each plate are filled with the reference concentration solution and the other three cylinders with the sample diluted in Solution 16 to a concentration approximating that of the reference calculated based on solution. This dilution is calculated based on the assumption that there was no loss of initial potency. After all the plates have incubated for 16 to 18 hours at 32°-35° C., the diameters of the zones of inhibition are measured using an appropriate measuring device such as a millimeter rule, calipers or an optical projector.

To estimate potency, the standard response line is prepared by averaging the diameters of the reference concentration and averaging the diameters of the standard response line concentration tested for each set of three plates. All 36 diameters of the reference concentration for all four sets of plates are also averaged. The average of the 36 diameters of the reference concentration is the correction point of the response line. The average diameter obtained for each concentration is corrected to the figure it would be if the average reference concentration diameter for that set of three plates was the same as the correction point. Thus, if in correcting the highest concentration of the response line (i.e. 0.16 units/mL), the average of the 36 diameters of the reference concentration is 16.5 millimeters and the average of the reference concentration of the set of three plates (the set containing 0.16 units/mL) is 16.3 millimeters, the correction is +0.2 millimeters. If the average reading of the highest concentration of the response line of these same three plates is 16.9 millimeters, the corrected diameter is then 17.1 millimeters. These corrected diameters, including the average of the 36 diameters of the reference concentration are plotted on 2-cycle semilog paper, using the concentration of the antibiotic in micrograms or units per mL as the ordinate (the logarithmic scale), and the diameter of the zone of inhibition as the abscissa. The response line is drawn either through these points by inspection or through points plotted for highest and lowest zone diameters obtained by means of the following equation:

$$L = \frac{3a + 2b + c - e}{5}$$

$$H = \frac{3e + 2d + c - a}{5}$$

where:

L=Calculated zone diameter for the lowest concentration of the standard response line;

H=Calculated zone diameter for the highest concentration of the standard response line c=Average zone diameter of 36 readings of the reference point standard solution;

a, b, d, e=Corrected average values for the other standard solutions, lowest to highest concentration, respectively.

To estimate the potency of the sample, the zone diameters of the standard are averaged and the zone diameters of the sample on the three plates are used. If the average zone diameter of the sample is larger than that of the standard, the difference between them is added to the reference concentration diameter of the standard response line. If the average zone diameter of the sample is lower than that of the standard, the difference between them is subtracted from the reference concentration diameter of the standard response line. From the response line, the concentrations corresponding to these corrected values of zone diameters are read. The concentration is then multiplied by the appropriate dilution factor to obtain the antibiotic content of the sample.

The following examples that further illustrate the invention are not to be construed as limiting the specification and claims in any way.

EXAMPLE 1

In view of the uncertainty of the stability of aqueous bleomycin solutions stored at room temperature (RT), a preliminary stability study was performed in which a bleomycin sulfate solution was monitored for drug stability after 24 months storage at RT. Bleomycin sulfate powder from Bristol Meyers Oncology Division was used for this and in subsequent experiments described below unless otherwise indicated. A test solution was prepared by diluting the powder in sterile water for injection (SWFI) to an initial concentration of 3 U/mL. The solution was tested for microbial potency after 24 months storage at RT using the microbial agar diffusion assay essentially as described in 21 C.F.R. §436.105. The only modification made to the assay was in testing duplicate preparations of a single drug lot (yielding 6 readings) per day and testing such duplicates on three separate days. Results from the six readings on each of the three separate testing days were then averaged to obtain the potency results. The results are shown in Table 1.

TABLE 1

| Interval (Months) | % of Initial Drug Remaining (Potency) |
| --- | --- |
| 0 | 100.0 |
| 24 | 48.0 |

Pharmaceutical solution formulations usually follow first-order decomposition kinetics (A. Martine, et al. Physical Pharmacy, Physical Chemical Principles in the Pharmaceutical Sciences. Lea & Febiger, Philadelphia, 3rd ed., 1983, page 359). The degradation rate constant and shelf-life of such preparations can be estimated using the relationship:

$$k = (2.303/t) \times \log[a/(a-x)] \qquad (1)$$

where "k" is the first-order degradation rate constant, "a" is the initial concentration or potency of test solution, and x is the loss in concentration or potency in time "t". Using the 24 month data, the degradation rate constant for bleomycin solution was estimated to be 0.03058/day. This data was then used to estimate shelf-life of bleomycin solution at RT, according to Eq. 1, as:

$$t_{90\%} = (2.303/k) \times \log[100/(100-10)]$$

where $t_{90\%}$ is the shelf-life of the product, i.e. the time required to reach 90% of the initial potency. Using the degradation rate value of 0.03058/day, the shelf-life of bleomycin solution at RT was estimated to be 3.44 months.

EXAMPLE 2

In view of the limited shelf-life estimated for a bleomycin sulfate solution at RT (see Example 1), further experiments were performed to determine if stability could be improved by storage at reduced temperature (5° C.). Bleomycin sulfate powder was solubilized in either 0.1M citrate buffer or SWFI to starting concentrations of 15.39 and 15.58 units per vial respectively. Citrate buffer was prepared as an 0.1M solution by dissolving 6.73 gm of citric acid, anhydrous (USP grade) and sodium citrate, dihydrate (USP grade) in a final total volume of 1 liter of SWFI. As controls, stability was also monitored on identical solutions (i.e. bleomycin sulfate in citrate buffer and SWFI) but stored at 25° C. and 40° C. Samples were tested for microbial potency after storage at the temperatures (in °C.) and for the time periods (in months) indicated below. All samples were tested for microbial potency using the microbial agar diffusion assay described in Example 1. The changes in potency of bleomycin sulfate stored in citrate buffer are indicated in Table 2a; changes in potency of bleomycin sulfate stored in water are indicated in Table 2b.

As shown in Table 2a, the potency of bleomycin sulfate in citrate buffer solution decreased by nearly 40% after 3 months storage at 40° C. Citrate solutions of bleomycin sulfate stored at lower temperatures, i.e. 25° C. and 5° C., showed little if any, decrease in stability after 3 months storage time. Results from Table 2b show a similar pattern of stability for the control (i.e. bleomycin sulfate solubilized in SWFI).

TABLE 2a

| Temp. (°C.) | Time (mo.) | Potency* | S.D.+ | % Potency Remaining** |
|---|---|---|---|---|
| 40 | 1 | 13.40 | 0.27 | 87.1 |
| 40 | 2 | 12.79 | 0.25 | 83.1 |
| 40 | 3 | 9.13 | 0.38 | 59.3 |
| 25 | 2 | 16.02 | 0.78 | 104.1 |
| 25 | 3 | 14.65 | 0.43 | 95.2 |
| 5 | 3 | 16.51 | 0.63 | 107.3 |

*Potency was determined by an average of six readings taken over a period of three days.
+S.D. = Standard deviation
**Percent potency remaining is the average potency at that interval divided by the initial average potency for the formulation.

TABLE 2b

| Temp. (°C.) | Time (mo.) | Potency* | S.D.+ | % Potency Remaining** |
|---|---|---|---|---|
| 40 | 1 | 14.97 | 0.59 | 96.1 |
| 40 | 2 | 15.22 | 0.46 | 97.7 |
| 40 | 3 | 9.88 | 0.42 | 63.4 |
| 25 | 2 | 16.38 | 0.43 | 105.1 |

TABLE 2b-continued

| Temp. (°C.) | Time (mo.) | Potency* | S.D.+ | % Potency Remaining** |
|---|---|---|---|---|
| 25 | 3 | 15.82 | 0.63 | 101.5 |
| 5 | 3 | 16.37 | 0.99 | 105.0 |

*, +, and**; As in Table 2a

EXAMPLE 3

Experiments were performed to determine the stability of bleomycin sulfate stored for up to 12 months at 5° C. in buffered or pH adjusted solutions. Samples of bleomycin sulfate powder were solubilized in acetate buffer, citrate buffer, and water adjusted to pH 4.6±0.1 for testing. The preparation of buffers used for solubilization was as follows:

1. Solution A: Acetate buffer was prepared by first dissolving 0.340 gm of sodium acetate trihydrate (U.S.P. grade) and 0.150 gm glacial acetic acid (reagent grade) in 400 mL of distilled water and then raising the volume with distilled water to a final quantity of 500 mL.
2. Solution B: Citrate buffer was prepared by dissolving 0.735 gm of sodium citrate, trisodium dihydrate, (U.S.P. grade) and 0.525 gm citric acid, monohydrate (reagent grade) in 400 mL of distilled water and then raising the volume with distilled water to a final quantity of 500 mL. The pH values of the final acetate and citrate solutions were measured as 4.6±0.1.
3. Solution C: Water (pH adjusted) was prepared by adjusting the pH of distilled water to 4.6±0.1 using a 0.01M sulfuric acid solution.

To prepare bleomycin solutions, 0.351±0.01 gm of bleomycin sulfate (Sicor; 1.71 units/mg) was dispensed into 150 mL of diluent in a suitable container and mixed slowly until dissolved. Solutions were adjusted to a final volume of 200 mL with the appropriate diluent and sterilized by passage through a 0.45 micron filter. A control solution of bleomycin (Solution D) was prepared identically to Solutions A, B and C but in water alone (i.e. not pH adjusted). Concentrations of bleomycin solutions prepared by this method were 16.11 units/vial for solution A, 15.94 units/vial for solution B, 16.29 units/vial for solution C and 16.12 units/vial for solution D. All samples were tested for potency as described in Example 1.

Table 3 shows the potency remaining after periods of 1, 3, 6 and 12 months storage at 5° C. in the indicated solutions. As shown in Table 3 the potency of bleomycin sulfate solutions stored at 5° C. remained relatively unchanged over time. The 5–10% variation seen in values over the 12 month time period reflects variability in the microbial assay itself. Potency values are expressed in units/vial.

TABLE 3

| | | Timed Stored at 5° C. | | | | | | | |
|---|---|---|---|---|---|---|---|---|---|
| Sample | Initial Units/vial | 1 month Units/vial | % activity remaining | 3 month Units/vial | % activity remaining | 6 months Units/vial | % activity remaining | 12 months Units/vial | % activity remaining |
| A | 16.11 | 15.57 | 96.6 | 14.74 | 91.5 | 15.13 | 93.9 | 15.96 | 99.0 |
| B | 15.94 | 16.12 | 101.1 | 15.03 | 94.3 | 14.91 | 93.5 | 15.64 | 98.1 |
| C | 16.29 | 15.46 | 94.9 | 14.24 | 87.4 | 14.89 | 91.4 | 15.31 | 93.9 |
| D | 16.12 | 15.43 | 95.7 | 14.59 | 90.5 | 15.10 | 93.7 | 15.56 | 96.5 |

We claim:

1. A method for maintaining stability of a stable bleomycin solution comprising storing said stable bleomycin solution at 2°–15° C. for at least about six months.

2. A method for maintaining stability of a stable bleomycin solution in accordance with claim 1, wherein said method further comprises adding an acetate buffer to said stable bleomycin solution.

3. A method for maintaining stability of a stable bleomycin solution in accordance with claim 1, wherein said method further comprises adding a citrate buffer to said stable bleomycin solution.

4. A method for maintaining stability of a stable bleomycin solution comprising storing said stable bleomycin solution at 2°–15° C. for at least about twelve months.

* * * * *